United States Patent [19]

Fritts

[11] Patent Number: 5,188,608

[45] Date of Patent: Feb. 23, 1993

[54] PROTECTIVE STABILIZING SLEEVE FOR IV NEEDLE

[76] Inventor: Mark A. Fritts, 2112 S. 24th St., Terre Haute, Ind. 47802

[21] Appl. No.: 862,464

[22] Filed: Apr. 2, 1992

[51] Int. Cl.$^5$ .............................................. A61M 5/32
[52] U.S. Cl. ............................ 604/179; 128/DIG. 26
[58] Field of Search .................... 604/174, 179, 180; 128/DIG. 26; 602/64, 61, 63

[56] References Cited

U.S. PATENT DOCUMENTS

| | | |
|---|---|---|
| 3,900,026 | 8/1975 | Wagner . |
| 4,275,721 | 6/1981 | Olson ................................. 604/180 |
| 4,309,991 | 1/1982 | DeMarco ............................. 602/64 |
| 4,470,410 | 9/1984 | Elliott ........................ 128/DIG. 26 |
| 4,591,356 | 5/1986 | Christie ............................. 604/179 |
| 4,799,923 | 1/1989 | Campbell ..................... 128/DIG. 26 |
| 4,822,342 | 4/1989 | Brawner . |
| 4,846,807 | 7/1989 | Safadago ............................. 604/179 |
| 4,870,976 | 10/1989 | Denny . |
| 4,898,587 | 2/1990 | Mera . |
| 4,961,418 | 10/1990 | McLaurin-Smith .................. 602/64 |
| 4,973,314 | 11/1990 | Garrett ............................... 604/180 |

Primary Examiner—Paul J. Hirsch
Attorney, Agent, or Firm—Woodard, Emhardt, Naughton Moriarty & McNett

[57] ABSTRACT

A protective stabilizing sleeve for an intravenous needle inserted into a vein in a patient's arm for protecting the site of the needle and stabilizing the connecting tube includes an outer fabric layer arranged with an interior layer of porous gauze material with a non-stick surface. In one arrangement VELCRO strips are disposed at the proximal and distal ends of the sleeve for securement of the sleeve around the arm. In a related embodiment the VELCRO strips are disposed along a longitudinal seam joining the two seam edges together. In a still further and related embodiment, the sleeve design is reshaped into a partial glove so as to protect and stabilize the IV needle and tube when inserted into the hand. The focus of the invention is on the design simplicity, the ease with which the sleeve or glove may be applied by the patient and the fact that both sleeve and glove designs are free of any type of exterior structural member which could conceivably be caught or bumped or hooked on some object thereby jarring or pulling the needle loose. By maintaining the exterior surface of the sleeve completely smooth and free of any other member the site of the needle remains clean and the risk of hooking the tube or bumping the needle is virtually eliminated. The sleeve and glove also provide a cushioning cover for the needle site.

10 Claims, 2 Drawing Sheets

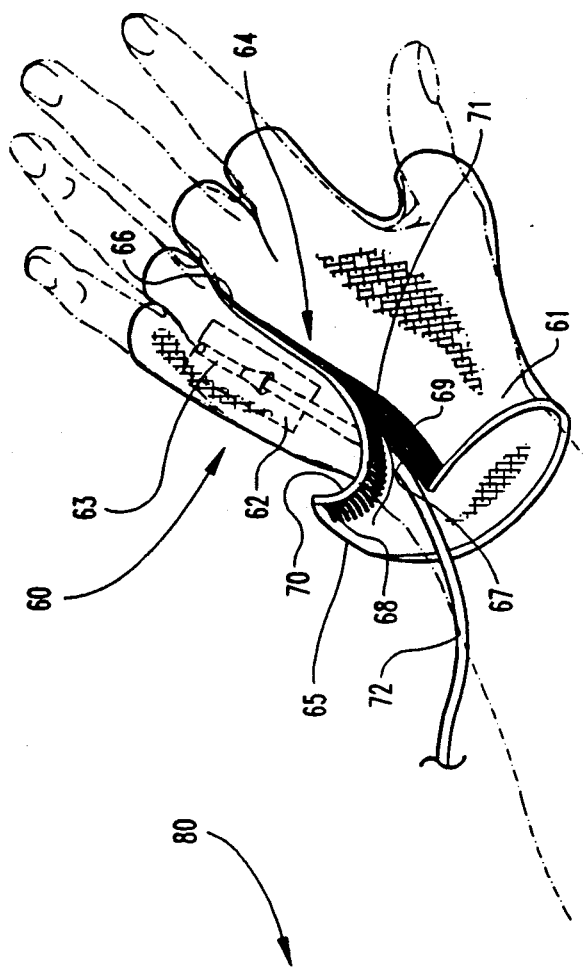
Fig. 3
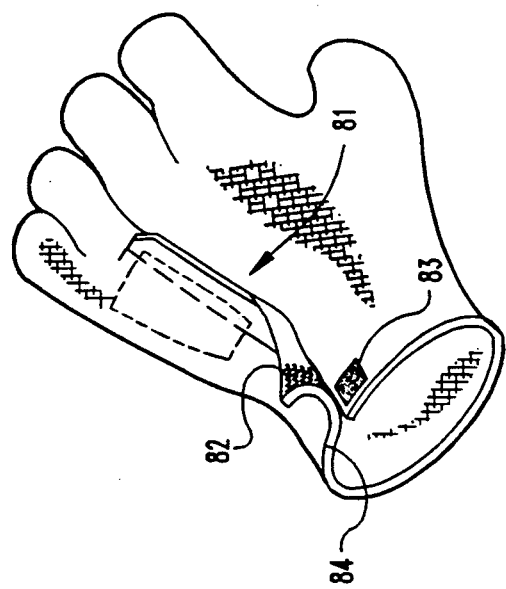
Fig. 4
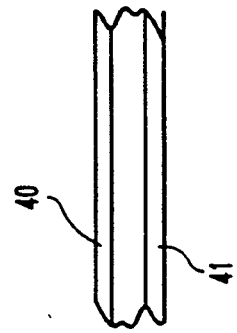
Fig. 5
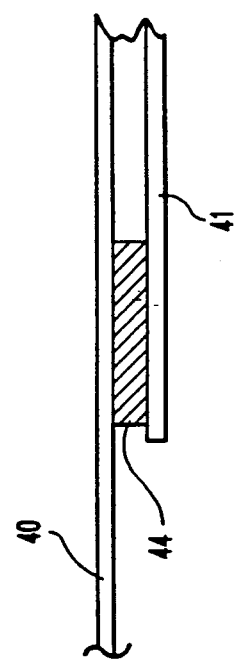

PROTECTIVE STABILIZING SLEEVE FOR IV NEEDLE

REFERENCE TO RELATED DOCUMENT

The present invention as disclosed herein has been submitted to the Patent and Trademark Office pursuant to the disclosure document program and disclosure number 296663 has been issued.

BACKGROUND OF THE INVENTION

The present invention relates in general to protective devices for intravenous (IV) needles which are inserted into a patient's vein, such as sleeves and covers. The present invention also relates to bands and straps used to secure and retain IV needles and the connecting tube to the needle.

More particularly the present invention relates to single devices which protect the IV needle from contamination while stabilizing the needle and connecting tube so that they cannot pull free from the patient's vein.

Intravenous needles provide a means to gradually inject liquids into a patient's vein. While the type of liquid may vary as will the reason for intravenous delivery, the basic structure and insertion into the patient is normally the same. The needle hub is connected to one end of a delivery tube and the opposite end of the delivery tube is connected to a reservoir supply of liquid. The rate of delivery from the reservoir supply can be controlled so as to achieve a desired volumetric flow rate for the particular patient and the particular liquid being administered. While occasionally the insertion of the needle into the patient's vein may be a hit or miss proposition, the nurse or other medical personnel eventually gets the needle properly inserted. Next the delivery tube is secured to the anatomy of the patient with adhesive tape in order to try and relieve any stress on the needle and to try to prevent or at least reduce the risk of the needle pulling out from the vein if the tube is pulled or catches on some object. In this normal arrangement, the needle is exposed to the atmosphere, except for the portion inserted into the vein, and thus any dirt, fluids or debris could contaminate the needle and tube at the site of insertion. In this arrangement there is also some discomfort associated with removal of the needle due to placing adhesive tape directly against the patient's skin.

Over the years others have attempted to design stabilizing bands for IV needles and the associated tube as well for holding and protecting the IV needles. Representative of some of these earlier attempts are the devices disclosed in the following issued patents:

| PATENT NO. | PATENTEE | ISSUE DATE |
| --- | --- | --- |
| 4,591,356 | Christie | May 27, 1986 |
| 4,822,342 | Brawner | April 18, 1989 |
| 4,898,587 | Mera | February 6, 1990 |
| 3,900,026 | Wagner | August 19, 1975 |
| 4,870,976 | Denny | October 3, 1989 |

Christie discloses an intravenous needle stabilizing band which wraps around the arm of the patient. The exterior surface of the band includes opposing flaps which open to permit passage over the tube part of the needle and means to secure the tube in place directly onto the exterior surface of the band.

Brawner discloses a prepared tape for a body inserted tube, such as an intravenous needle. The device includes a multi-layer arrangement typically involving two separate portions as is illustrated in FIG. 4 for clamping the hub of the needle and for securing the delivery tube. In this instance as has been explained in the background discussion, the tape goes directly to the patient's skin and portions of the needle as well as the delivery tube are both exposed to the atmosphere and create surfaces which may be caught or pulled with normal movement.

Mera discloses an intravenous line stabilizing device configured as a two-part clamping arrangement which has a specifically contoured shape to provide a clearance slot for the needle hub and a channel for the tube. Once the base plate is secured directly to the patient's arm the needle hub and tube are laid into position and a top cover or clamping plate is placed on top. A second clamp is used to secure the tube to the arm of the patient and the run of tubing up the arm from the needle location to this securing clamp location is open and free to be caught or pulled by movement of the hand thereby running the risk that the needle could be pulled loose from the vein.

Wagner discloses a somewhat complicated device for holding and protecting intravenous injection needles. As is illustrated in FIGS. 1 and 2, there is a cap member 15 which is applied directly to the arm and has an angled neck portion 17 for securing the needle hub and tube in an inclined and upwardly elevated orientation. All of the attention of this reference is directed to maintaining some angularity of the needle and stabilizing the needle hub without regard to the tube or where the tube will run. Consequently, as the loose tube is allowed to move freely there is a chance that it would be caught or pulled by some object within the patient's room or wherever the patient may be moving. If the tube is caught, the needle could be jarred loose or at least create substantial discomfort for the patient.

Denny discloses a very elaborate intravenous injection shield assembly which includes a protective shield member made of a rigid transparent plastic. The assembly further includes strap members for holding the assembly in a predetermined position on a limb and defines a clearance space which is suitable to receive an intravenous needle and tubing. The disclosed design is somewhat complex with a number of straps and ties which must be completed as well as having substantial size and weight and clearly not providing the type of device which could be easily applied and removed.

While some of the structural concepts of these listed references relate to stabilizing the needle and tube and while some references disclose partial covering of the needle, none are believed to anticipate the present invention. Further, the simplicity of the present invention and the additional enhancements provided would not have been obvious in view of the above-listed references. Additionally, the listed references all pertain to insertion of the needle into a vein in a patient's arm or back of the hand adjacent the wrist. What is not disclosed and what each device that is disclosed in the listed references is not suitable for is to stablize and protect the needle and tube when the needle is inserted into the vicinity of the metacarpo-phalangeal joint. The difficulty with this area is the extent of flexing of the fingers and hand for performing basic mechanical motions such as when eating. There is not a suitably flat stationary surface adjacent the point of insertion of the needle to utilize devices such as that disclosed in Mera which need a flat stationary surface for the designed method of attachment. Although Mera describes its base plate 12 as being of a moderately pliable plastic, its pliability is directed only to contouring to the skin. There is no suggestion that this base plate will stretch in length so as to conform to the stretched skin over the metacarpo-phalangeal joint during maximum flexing (closing) of the hand. In contrast, the present invention discloses a design embodiment which is suitable for IV needles inserted into the area of the hand adjacent the metacarpo-phalangeal joint.

SUMMARY OF THE INVENTION

A protective stabilizing sleeve for an intravenous needle inserted into a vein according to one embodiment of the present invention comprises an outer fabric layer having proximal and distle ends and an exterior surface therebetween, the outer fabric layer being arranged to cover the needle and a portion of the tube which connects the needle to a supply of liquid, the tube exiting from beneath the proximal end of the outer fabric layer, the exterior surface of the outer fabric layer being free of any structural members. The protective stabilizing sleeve further includes an inner layer attached to the outer layer and positioned for placement over the needle location and securement means disposed at the proximal end of the outer fabric layer for securing the sleeve around the arm of the patient and stabilizing the exiting tube.

One object of the present invention is to provide an improved protective stabilizing sleeve for an intravenous needle.

Related object and advantages of the present invention will be apparent from the following description.

BRIEF DESCRIPTION OF THE DRAWINGS

FIG. 3 is a top plan view of a protective stabilizing glove for an intravenous needle inserted into a patient's hand according to a typical embodiment of the present invention.

FIG. 4 is a top plan view of an alternative style of protective stabilizing glove according to the present invention.

FIG. 5 is a side elevational view in full section illustrating the material lamination construction for the various embodiments of the present invention.

DESCRIPTION OF THE PREFERRED EMBODIMENT

Figure 2:
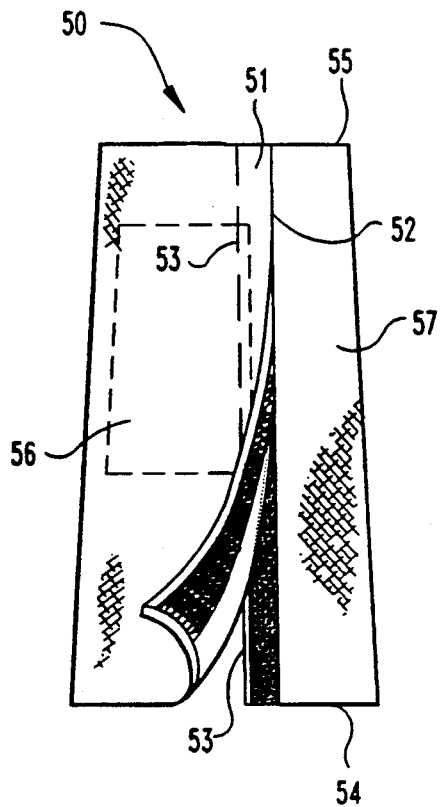
FIG. 2 is a top plan view of a second embodiment of a protective stabilizing sleeve according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
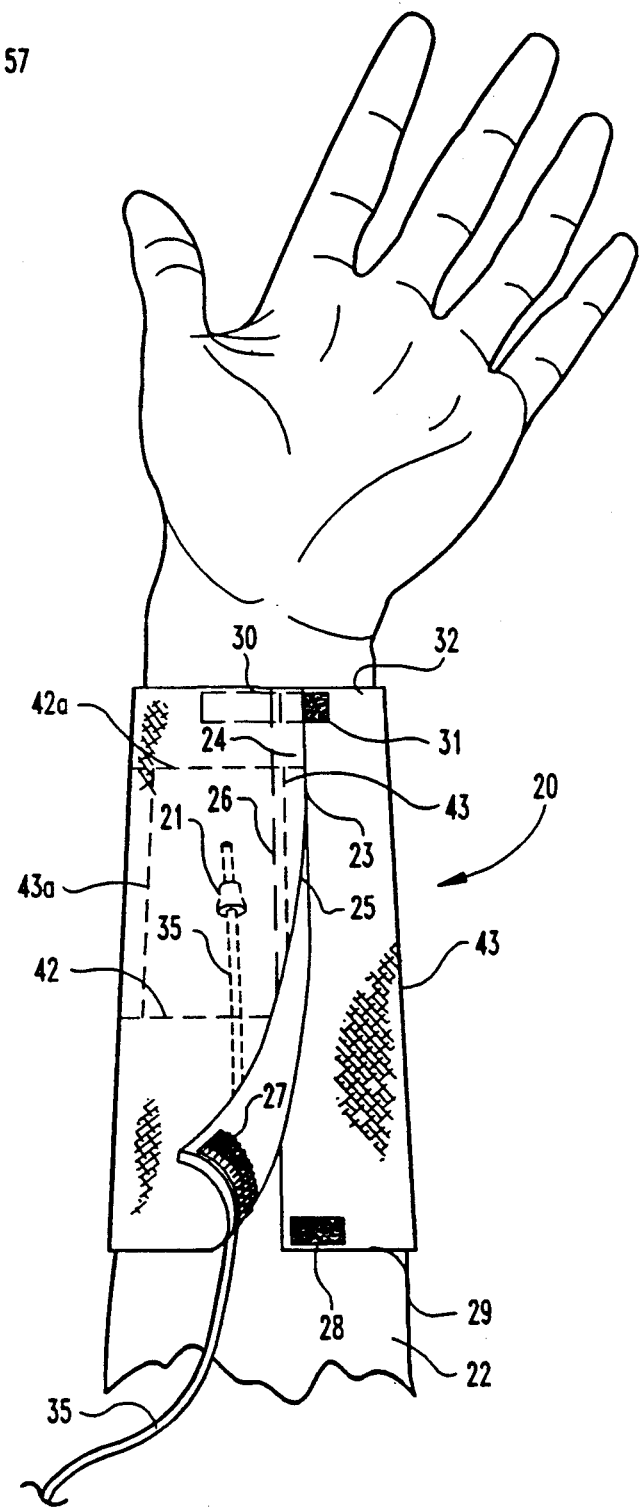
FIG. 1 is a top plan view of a protective stabilizing sleeve for an intravenous needle applied to a patient's arm according to a typical embodiment of the present invention.

Referring to FIG. 1 there is illustrated a protective stabilizing sleeve 20 for intravenous (IV) needle 21 which is inserted into a vein in the arm 22 of the patient. As the name implies the sleeve 20 provides both protection for the needle 21 and stabilizing of the needle.

There are two important concerns in the use of IV needles. One concern is the cleanliness of the site and the desire to keep the site free from any type of dirt, debris or contaminants. The other concern relates to stabilizing the needle and connecting tube so that with normal use of the hand and arm the needle will not dislodge or come loose. Stabilizing of the tube also helps to guard against the tube being caught or pulled and as a result pulling the needle loose.

The tube from the needle connects to an IV bag or bottle (not illustrated) and thus there is some length of tubing, often significant, stretching through the air from the needle to the fluid supply reservoir. With the normal activity of the patient as well as of the medical or treatment personnel moving in and around the patient, there is a risk of some object catching or hooking the tube portion which is free and as a result giving the needle a tug or jerk. If the force is sufficient, the needle can actually be pulled free from the patient's arm or hand.

In the present invention protective stabilizing sleeve 20 is configured and sized to wrap around the arm 22 and completely cover the site of needle 21. Sleeve 20 has a slightly tapering design in recognition that the arm, from the wrist to the elbow, has a slight increase in diameter size. Split, open seam 23 extends the full length of the sleeve and the circumferential size of the sleeve is large enough to provide an area 24 of overlap, even for large patients. Sleeve edges 25 and 26 which create seam 23 are not otherwise connected except at their ends. Each end of the sleeve is arranged with mating VELCRO strips in a mating combination of hook-like and loop-like projections. Strips 27 and 28 are disposed at proximal end 29 and strips 30 and 31 are disposed at distal end 32. Strips 27 and 30 provide the hook-like projection and strips 28 and 31 provide the loop-like projections. Strips 28 and 31 which are secured to the outer surface of sleeve 20 are relatively short in length. Strips 27 and 30 which are secured to the inside surface of sleeve 20 are relatively long in length. This specific arrangement of the VELCRO strips allows the patient to selectively control how tight the sleeve will be around the arm at the distal end as well as at the proximal end. Since end 29 is where tube 35 exits from beneath the sleeve, it is desired to tightly secure the sleeve around the arm at this location in order to anchor the tube 35 to the arm and thereby stablize the needle. Any force on the tube will stop at end 29 of the sleeve and the sleeve will absorb the force without the needle being jarred loose or jerked which would be painful and could cause the needle to have to be reset.

The pressure on needle 21 exerted by sleeve 20 can be adjusted in one of two ways. The tightness of the VELCRO securement at ends 29 and 32 will have some effect on the sleeve pressure on the needle even though edges 25 and 26 are not otherwise connected. Another way to reduce the pressure of sleeve on the needle is to put ends 29 and 32 closer together along the arm. This arrangement of pushing the ends closer together provides extra sleeve material in the region of needle 21 and with surplus material there is little or no pressure on the needle.

Sleeve 20 is a two-layer lamination in part (see FIG. 5), with an outer layer 40 fabricated out of a cloth, polyester and elastic blend and a smaller or partial non-stick porous gauze layer 41. Layer 41 is bounded by edge lines 42, 42a, 43 and 43a and is selectively sized and positioned to cover and be centered over the site of the needle. Since layer 41 is provided primarily for the protection and cleanliness of needle 21, the gauze layer does not need to extend the full length of the sleeve nor the full width. The porous gauze layer 41 is a material similar to that currently used with non-stick bandages that allow the site to remain sterile while providing absorption of any blood or other body fluid without sticking to any opening or wound.

By placing a plurality of VELCRO pads 44 with hook-like projections on the outer layer 40 in the area where gauze layer 41 will be placed, the gauze layer may be made removable. The porous nature of the gauze layer 41 enables it to hook onto the projections of the VELCRO pads 44. If layer 41 becomes contaminated it can be removed, discarded and replaced. The outer layer 40 can be washed as needed and thereafter a new non-stick gauze layer reapplied by reusing the same VELCRO pads 44.

One advantage of the design of sleeve 20 compared to earlier devices and concepts is the fact that the interior sleeve 20 is completely free of any tube tie-downs, clamps, brackets, holders, tape layers, raised portions or other protuberances, or structural elements. The exterior surface is smooth and clean and there is nothing on the outer sleeve surface to get bumped, hit, caught, pulled or jarred and nothing to come loose. The sleeve material is flexible and lightweight and is quickly and easily put around the arm, after the needle is inserted into a vein, with a minimum of effort and discomfort to the patient. The sleeve can be applied by the patient unlike some of the earlier devices which are significantly more complex and elaborate. Part of the novelty of the present invention is the recognition of simplicity and a realization that the earlier complex designs are not needed.

Referring to FIG. 2 a variation to sleeve 20 is illustrated. Sleeve 50 is virtually identical to sleeve 20 with two exceptions. First, the free edges 25 and 26 of sleeve 20 are now fitted with cooperating longitudinal strips of VELCRO. The area of VELCRO overlap and edge to edge securement is identified as rectangular region 51. The underside of top edge 52 is fitted with one half of the VELCRO assembly and the top surface of lower edge 53 is fitted with the other half of the VELCRO assembly. The circumferential length (i.e., width) of one half of the VELCRO assembly controls the degree of size adjustment and sleeve tightness. As to the second exception, there are no circumferential VELCRO strips extending along ends 54 and 55. Sleeve 50 still includes a non-stick gauze layer 56 and uses the same material as sleeve 20 for the outer sleeve layer 57.

As long as the IV needle is inserted into the vein in the arm, a number of needle stabilizing designs may be suitable. While the simplicity of the present invention, including the lack of any structural element on the exterior of the sleeve, is believed to be an advantage over prior devices, the prior devices still work on the arm. What happens though when the needle is to be inserted into a vein in the hand? Devices which employ a sleeve-type arrangement must wrap around the entire hand including the thumb. This completely debilitates the hand making it virtually useless to perform any basic maneuvers.

Devices which require a relatively flat, stationary surface are also unable to be used for hand IV needles as the flexing of the fingers for basic movements, disrupts any flat, stationary surface. The point to note is that the needle will typically be inserted in an area between the fingers and near the metacarpo-phalangeal joint. When the hand is opened and the fingers extended, this top surface area of the hand is flat and the skin is somewhat loose. However, with movement of the fingers to close the hand, such as to grasp or hold, the joint flexes creating an inverted V-shaped surface with the metacarpal bone inclined upwardly and the phalanx inclined downwardly. This movement also stretches the skin causing this distance between two points on the back of the extended hand to actual increase slightly in length on the closed hand. However, more importantly the joint (knuckle) protrudes upwardly eliminating any flat surface.

Devices which must have a somewhat stationary and flat surface for mounting simply will not work for IV needles inserted into this area of the hand. In order to address this concern the present invention takes the simplicity of sleeves 20 and 25 which are free of any exterior structures and transfers those design ideas into a fingerless or partial glove as illustrated in FIGS. 3 and 4.

Glove 60 is partially informed so that the fingers and thumb are exposed and able to be used normally. The glove terminates at one end just short of the interphalangeal joint of each digit and at the other end at the wrist. Glove 60 is made from the same material as sleeves 20 and 50 and includes both an outer layer 61 and a non-stick gauze layer 62. The size of the gauze layer is such that it covers the area of the needle 63 and layer 62 is removable so that the glove can be washed and reused by attaching a new, sterile gauze layer. VELCRO pads of hook-like projections, such as pads 44, are used to removably attach the gauze layer 62 to the outer layer 61.

Glove 60 is a full glove in all other respects, including a full palm. In order to minimize any disruption to needle 63 when the glove is put on, a full length slit 64 is made from end 65 to the base between the third and fourth digits. The free edges 66 and 67 created by this slit are fitted with cooperating strips 68 and 69 of VELCRO to close the glove after it is put onto the hand.

As should be understood, with the needle inserted, the left side flap 70 is gently folded over and closed against the right side flap 71. The specific placement of the VELCRO strips is optional. The left side flap may go on top of the right side flap, or the reverse. As illustrated, gauze layer 62 is sized and arranged completely on the underside of the left flap so that a single gauze layer can be used without interference from slit 64. Securement of the VELCRO strips and the close sizing of end 65 to the size of the wrist provides the desired stablization of the needle by clamping tube 72 in place.

In FIG. 4 a slight variation to glove 60 is illustrated. Glove 80 is identical to glove 60 in every respect except slit 81 does not include VELCRO and the edges which overlap are not attached to one another along their full length. Securement and thus stabilizing of the tube and needle is achieved by two VELCRO strips 82 and 83 which are secured along end edge 84. This arrangement is virtually the same as that described for sleeve 20 with regard to strips 27, 28 at end 29 and strips 30 and 31 at end 32.

It is also to be understood that in lieu of fabricating sleeve 20 out of a fabric which can be washed and reused, one could use a disposable material similar to the paper material used for disposable gowns and masks. This same disposable paper material could be used for the design of partial gloves 60 and 80. When a disposable paper or other disposable material is used the porous gauze layer would not have to be provided as a removable element but could simply be bonded or sewn directly to the outer sleeve layer as it would be disposed of along with the sleeve. With a disposable material the VELCRO strips could be adhesively bonded to the surfaces and as would be contemplated, the various VELCRO strips can be replaced by adhesive means or mechanical fasteners such as snaps. It is also envisioned that a drawstring style of securement could be used for sleeve 20 and for glove 80. Finally, the VELCRO strips which are used with the fabric layers are secured in place by either the use of a bonding adhesive or are sewn to the fabric material at the appropriate locations.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A protective stabilizing sleeve for an intravenous needle inserted into a vein in a patient's arm, said needle being connected to a supply of liquid by a tube, said protective stabilizing sleeve comprising:
   an uninterrupted outer fabric panel having proximal and distal ends and an exterior surface therebetween, said outer fabric panel being arranged when wrapped around said arm to cover said needle and a portion of said tube, the tube exiting from beneath said proximal end, said exterior surface being free of any structural members and said panel being free of any opening, said panel tapering from the proximal end to the distal end;
   an inner layer of gauze attached to the outer fabric panel and positioned for placement over the needle location; and
   securement means disposed only at the proximal and distal ends of said outer fabric panel for securing said sleeve around the arm and stabilizing the exiting tube.

2. The protective stabilizing sleeve of claim 1 wherein said securement means includes a mating strip combination of hook-like and loop-like projections.

3. A protective stabilizing sleeve for an intravenous needle inserted into a vein in a patient's arm, said needle being connected to a supply of liquid by a tube, said protective stabilizing sleeve comprising:
   an outer uninterrupted fabric panel having proximal and distal ends and an exterior surface therebetween, said outer fabric panel being arranged when wrapped around said arm to cover said needle and a portion of said tube, the tube exiting from beneath said proximal end, said exterior surface being free of any structural members and said panel being free of any opening, said panel tapering from the proximal end to the distal end;
   an inner layer of gauze attached to the outer fabric panel and positioned for placement over the needle location; and
   securement means extending from said proximal end to said distal end for securing said sleeve around the arm and stabilizing the exiting tube.

4. The protective stabilizing sleeve of claim 3 wherein said securement means includes a mating strip combination of hook-like and loop-like projections.

5. A protective stabilizing glove for an intravenous needle inserted into a vein in a patient's hand, said needle being connected to a supply of liquid by a tube, said protective stabilizing glove comprising:
   an outer fabric panel having a wrist end, a distal end configured with partial digit sleeves and an exterior surface therebetween, said outer fabric panel being arranged to slide over the digits of the hand and to cover said needle and a portion of said tube, the tube exiting from beneath the outer fabric panel at said wrist end, said exterior surface being free of any structural members and said panel being free of any other opening;
   an inner layer of gauze attached to said outer fabric panel and positioned for placement over the needle location; and
   securement means extending from said wrist end to said distal end for securing said glove on the hand of the patient and stabilizing the exiting tube.

6. The protective stabilizing glove of claim 5 wherein said securement means includes a mating strip combination of hook-like and loop-like projections.

7. The protective stabilizing glove of claim 5 wherein said glove is full form around the back of the hand and palm area and is modified into partial form by terminating the glove in the vicinity of the interphalangeal joint of each digit.

8. A protective stabilizing glove for an intravenous needle inserted into a vein in a patient's hand, said needle being connected to a supply of liquid by a tube, said protective stabilizing glove comprising:
   an outer fabric panel having a wrist end, a distal end configured with partial digit sleeves and an exterior surface therebetween, said outer fabric panel being arranged to slide over the digits of the hand and to cover said needle and a portion of said tube, the tube exiting from beneath the outer fabric panel at said wrist end, said exterior surface being free of any structural members and said panel being free of any other opening;
   an inner layer of gauze attached to said outer fabric panel and positioned for placement over the needle location; and
   securement means disposed at the wrist end of said outer fabric panel for securing said glove onto the hand and stabilizing the exiting tube.

9. The protective stabilizing glove of claim 8 wherein said securement means includes a mating strip combination of hook-like and loop-like projections.

10. The protective stabilizing glove of claim 8 wherein said glove is full form around the back of the hand and palm area and is modified into partial form by terminating the glove in the vicinity of the interphalangeal joint of each digit.

* * * * *